United States Patent
Süss-Fink et al.

(10) Patent No.: US 7,015,358 B2
(45) Date of Patent: Mar. 21, 2006

(54) PROCESS FOR THE PRODUCTION OF KETONES

(75) Inventors: Georg Süss-Fink, Neuchâtel (CH); Georgiy B Shul'Pin, Moscow (RU); Lidia S. Shul'Pina, Moscow (RU)

(73) Assignee: Lonza AG, Basel (CH)

( * ) Notice: Subject to any disclaimer, the term of this patent is extended or adjusted under 35 U.S.C. 154(b) by 0 days.

(21) Appl. No.: 10/476,025

(22) PCT Filed: Apr. 23, 2002

(86) PCT No.: PCT/EP02/04440

§ 371 (c)(1),
(2), (4) Date: Oct. 27, 2003

(87) PCT Pub. No.: WO02/088063

PCT Pub. Date: Nov. 7, 2002

(65) Prior Publication Data

US 2004/0138506 A1 Jul. 15, 2004

Related U.S. Application Data

(60) Provisional application No. 60/286,539, filed on Apr. 27, 2001.

(30) Foreign Application Priority Data

May 15, 2001 (EP) .......................................... 01111776

(51) Int. Cl.
*C07C 45/29* (2006.01)

(52) U.S. Cl. ...................... 568/351; 568/354; 568/361; 568/385; 568/391

(58) Field of Classification Search ................. 568/351, 568/354, 361, 385, 391
See application file for complete search history.

(56) References Cited

U.S. PATENT DOCUMENTS 5,246,621 A * 9/1993 Favre et al. ............ 252/186.33
6,620,972 B1 * 9/2003 Crich et al. .................... 568/27

FOREIGN PATENT DOCUMENTS

DE          10024617          12/2000

OTHER PUBLICATIONS

Wieghardt et al., J. Am. Chem. Soc., 1988, 110, p. 7398–7411.
J.R.L. Smith, G.B. Shul'pin, Tetrahedron Lett. 39 (1998) 4909–4912.

* cited by examiner

*Primary Examiner*—Johann Richter
*Assistant Examiner*—Sikarl A. Witherspoon
(74) *Attorney, Agent, or Firm*—Fisher, Christen & Sabol

(57) ABSTRACT

A process for the production of aliphatic or alicyclic monoketones or alicyclic diketones of the formula $R^1-C(=O)-R^2$ in which $R^1$ is a linear or branched $C_{1-10}$-alkyl group and $R^2$ is a linear or branched $C_{1-10}$-alkyl group or a phenyl group, or $R^1$ or $R^2$ together are $-(CH_2)_m-[C(=O)]_n-(CH_2)_p-$, wherein m and p independently are integers from 1 to 4 and n is 0 or 1, thus forming an alicyclic ring together with the carbonyl group of $R^1-C(=O)-R^2$ by oxidizing a secondary alcohol of formula $R^{1'}-CHOH-R^{2'}$ in which $R^{1'}$ and $R^{2'}$ either have the same meaning as $R^1$ and $R^2$ above or, if $R^1$ and $R^2$ together are $-(CH_2)_m-[C(=O)]_n-(CH_2)_p-$, are together $-(CH_2)_m-(CHOH)_n-(CH_2)_p-$ wherein m, n and p are as defined above, with a peroxy compound in the presence of a carboxylic acid and a manganese(IV) complex of 1,4,7-trimethyl-1,4,7-triazacyclononane.

25 Claims, No Drawings

PROCESS FOR THE PRODUCTION OF KETONES

This application is a 371 national stage application of International (PCT) Application No. PCT/EP02/04440, filed on Apr. 23, 2002, that has priority benefit of European Patent Application No. 01111776.9 filed on May 15, 2001, that has priority benefit of U.S. Provisional Patent Application No. 60/286,539 filed on Apr. 27, 2001.

The invention relates to a process for the production of aliphatic and alicyclic ketones by oxidizing the corresponding secondary alcohols with a peroxy compound in the presence of a catalyst.

The ketones obtainable by the process of the invention have the general formula

$$R^1-C(=O)-R^2 \quad (I)$$

in which $R^1$ is a linear or branched $C_{1-10}$-alkyl group and $R^2$ is a linear or branched $C_{1-10}$-alkyl group or a phenyl group, or $R^1$ and $R^2$ together are $-(CH_2)_m-[C(=O)]_n-(CH_2)_p-$, wherein m and p independently are integers from 1 to 4 and n is 0 or 1, thus forming an alicyclic ring together with the carbonyl group of (I).

These ketones are valuable compounds for a large number of applications, for example as solvents, building blocks for organic syntheses, fragrances etc.

Linear or branched $C_{1-10}$-alkyl groups are, for example, methyl, ethyl, propyl, isopropyl butyl, isobutyl, sec-butyl, tert-butyl pentyl, 2-methylbutyl, 3-methylbutyl, 2,2-dimethylpropyl, hexyl, heptyl, octyl, nonyl and decyl, including all isomers of these groups. The ketones wherein $R^1$ and $R^2$ together are a group of the formula $-(CH_2)_m-[C(=O)]_n-(CH_2)_p-$ are in particular all alicyclic monoketones having 3 to 9 ring carbon atoms or diketones having 4 to 10 carbon atoms wherein the carbonyl groups are separated by at least one methylene group. These alicyclic ketones include cyclopropanone, cyclobutanone, cyclopentanone, cyclohexanone, cycloheptanone, cyclooctanone, cyclononanone, 1,3-cyclobutanedione, 1,3-cyclopentanedione, 1,3-cyclohexanedione, 1,4-cyclohexanedione, 1,3-cycloheptanedione, 1,4-cycloheptanedione, 1,3-cyclooctanedione, 1,4-cyclooctanedione, 1,5-cyclooctanedione, 1,3-cyclononandione, 1,4-cyclononanedione, 1,5-cyclononanedione, 1,3-cyclodecanedione, 1,4-cyclodecanedione, 1,5-cyclodecanedione and 1,6-cyclodecanedione.

While some of the above mentioned ketones (I) are being produced by the chemical industry in large amounts (e. g. acetone, cyclohexanone) using processes giving good yields, some others are only available by tedious procedures and/or in poor yields. The object of the present invention was to provide a versatile process for the production of these ketones in good yields and without expensive reactants.

According to the invention, this has been accomplished by the process of claim 1.

It has been found that secondary alcohols of the formula

$$R^{1'}-CHOH-R^{2'} \quad (II)$$

in which $R^{1'}$ and $R^{2'}$ either have the same meaning as $R^1$ and $R^2$ above or, if $R^1$ and $R^2$ together are $-(CH_2)_m-[C(=O)]_n-(CH_2)_p-$ (i.e., if the product is a alicyclic diketone), are together $-(CH_2)_m-(CHOH)_n-(CH_2)_p-$ wherein m, n and p are as defined above, can smoothly be oxidized by peroxy compounds in the presence of a carboxylic acid and a manganese(IV) complex of 1,4,7-trimethyl-1,4,7-triazacyclononane (Me$_3$tacn) to give the corresponding ketones (I) in good to excellent yields.

Preferred peroxy compounds are hydrogen peroxide and peroxycarboxylic acids and mixtures thereof. It should be noted that hydrogen peroxide reacts with carboxylic acids to give peroxycarboxylic acids in an equilibrium reaction.

It is also possible to use other peroxy compounds, for example, tert-butyl hydroperoxide.

The most preferred carboxylic acid is acetic acid.

The preferred manganese(IV) complex of Me$_3$tacn is the dinuclear complex $[(Me_3tacn)_2Mn_2O_3]^{2+}[PF6]_2^-$ with three bridging oxo ligands [=tri-$\mu$-oxobis(1,4,7-trimethyl-1,4,7-triazacyclononane)dimanganese bis(hexafluorophosphate)] which has been described by K. Wieghardt et al., *J. Am. Chem. Soc.* 1988, 110, 7398.

The process according to the invention may be carried out in polar aprotic solvents such as acetonitrile, nitromethane or mixtures thereof, acetonitrile being especially preferred.

A particularly preferred application of the process of this invention is the production of 1,4-cyclohexanedione (I; $R^1,R^2=-(CH_2)_m-[C(=O)]_n-(CH_2)_p-$, m=p=2, n=1) from 1,4-cyclohexanediol (II; $R^{1'},R^{2'}=-(CH_2)_m-(CHOH)_n-(CH_2)_p-$, m=p=2, n=1) which is easily available from hydroquinone.

The process of the invention may be carried out at or near room temperature, e. g., at 0–40° C., the reaction times being typically a few hours or less. The work-up can be done according to methods well known in the art, preferably after addition of a suitable reducing agent to destroy any excess of peroxy compound in order to avoid further oxidation and potential explosion hazards.

The invention is illustrated by the following non-limiting examples.

EXAMPLE 1

Preparation of 1,4-Cyclohexanedione

To a solution of 0.5 g of 1,4-cyclohexanediol in 10 ml of acetonitrile were added 0.2 ml of a 6.32 mM acetonitrile solution of $[(Me_3tacn)_2Mn_2O_3][PF_6]_2$ and 0.4 ml of acetic acid (99%). A mixture of 2 ml of a 35% aqueous hydrogen peroxide solution in 11 ml of acetonitrile was added dropwise under vigorous sting at 23° C. within one hour. After the addition the clear solution was stirred for additional 30 minutes, all volatiles removed in vacuo and the residue analysed by gas chromatography, $^1$H- and $^{13}$C NMR spectroscopy, showing >99% conversion and >99% selectivity. The analyses were compared with a commercially available (Fluka) sample of 1,4-cyclohexanedione.

EXAMPLES 2–9

In a procedure similar to that of example 1, several secondary alcohols were oxidized In each case, a reaction mixture containing 0.23 M (1 M=1 mol/l) of the respective alcohol, 1.0 M of hydrogen peroxide, 0.4×10$^{-4}$ M of $[(Me_3tacn)_2Mn_2O_3][PF_6]_2$ and 0.5 M of acetic acid in acetonitrile as solvent was reacted at 20° C. for 3 h. The yields of the products were measured by gas chromatography after treatment of the samples with triphenylphosphine. The results are given in Table 1. All yields are based on the initial amounts of alcohol.

TABLE 1

| Example | Alcohol | Conversion [%] | Product | Yield [%] |
|---|---|---|---|---|
| 2 | 2-propanol | 100 | acetone | 98 |
| 3 | 2-butanol | 100 | 2-butanone | 98 |
| 4 | 2-pentanol | 99 | 2-pentanone | 97 |
| 5 | 3-pentaaol | 98 | 3-pentanone | 97 |
| 6 | 3-methyl-2-butanol | 100 | 3-methyl-2-pentanone | 100 |
| 7 | 3-hexanol | 97 | 3-hexanone | 96 |
| 8 | cyclohexanol | 95 | cyclohexanone | 91 |
| 9 | 1-phenylethanol | ≈100 | acetophenone | ≈100 |

What is claimed is:

1. A process for the production of an aliphatic or alicyclic monoketone or an alicyclic diketone of the formula:

$$R^1—C(=O)—R^2 \quad (I)$$

in which $R^1$ is a linear or branched $C_{1-10}$-alkyl, and $R^2$ is a linear or branched $C_{1-10}$-alkyl or a phenyl, or $R^1$ or $R^2$ together are $—(CH_2)_m—[C(=O)]_n—(CH_2)_p—$, wherein m and p independently are integers from 1 to 4 and n is 0 or 1, thus forming an alicyclic ring together with the carbonyl group of (I), by oxidizing a secondary alcohol of formula $$R^{1'}—CHOH—R^{2'} \quad (II)$$

in which $R^{1'}$ and $R^{2'}$ either have the same meaning as $R^1$ and $R^2$ above or, if $R^1$ and $R^2$ together are $—(CH_2)_m—[C(=O)]_n—(CH_2)_p—$, are together $—(CH_2)_m—(CHOH)_n—(CH_2)_p—$ wherein m, n and p are as defined above, with a peroxy compound in the presence of a carboxylic acid and a manganese(IV) complex of 1,4,7-trimethyl-1,4,7-triazacyclononane.

2. The process of claim 1 wherein the peroxy compound is selected from the group consisting of hydrogen peroxide and peroxycarboxylic acids and mixtures thereof.

3. The process of claim 1 wherein the carboxylic acid is acetic acid.

4. The process of claim 1 wherein the manganese(IV) complex of 1,4,7-trimethyl-1,4,7-triazacyclononane is tri-μ-oxobis(1,4,7-trimethyl-1,4,7-triazacyclononane)-dimanganese bis(hexafluorophosphate).

5. The process of claim 1 wherein the oxidation is conducted in a solvent selected from the group consisting of acetonitrile, nitromethane, and mixtures thereof.

6. The process of claim 1 wherein $R^1$ and $R^2$ together are $—(CH_2)_2—C(=O)—(CH_2)_2—$ and $R^{1'}$ and $R^{2'}$ together are $—(CH_2)_2—CHOH—(CH_2)_2—$.

7. The process of claim 2 wherein the carboxylic acid is acetic acid.

8. The process of claim 2 wherein the manganese(IV) complex of 1,4,7-trimethyl-1,4,7-triazacyclononane is tri-μ-oxobis(1,4,7-trimethyl-1,4,7-triazacyclononane)-dimanganese bis(hexafluorophosphate).

9. The process of claim 3 wherein the manganese(IV) complex of 1,4,7-trimethyl-1,4,7-triazacyclononane is tri-μ-oxobis(1,4,7-trimethyl-1,4,7-triazacyclononane)-dimanganese bis(hexafluorophosphate).

10. The process of claim 2 wherein the oxidation is conducted in a solvent selected from the group consisting of acetonitrile, nitromethane, and mixtures thereof.

11. The process of claim 3 wherein the oxidation is conducted in a solvent selected from the group consisting of acetonitrile, nitromethane, and mixtures thereof.

12. The process of claim 4 wherein the oxidation is conducted in a solvent selected from the group consisting of acetonitrile, nitromethane, and mixtures thereof.

13. The process of claim 2 wherein $R^1$ and $R^2$ together are $—(CH_2)_2—C(=O)—(CH_2)_2—$ and $R^{1'}$ and $R^{2'}$ together are $—(CH_2)_2—CHOH—(CH_2)_2—$.

14. The process of claim 3 wherein $R^1$ and $R^2$ together are $—(CH_2)_2—C(=O)—(CH_2)_2—$ and $R^{1'}$ and $R^{2'}$ together are $—(CH_2)_2—CHOH—(CH_2)_2—$.

15. The process of claim 4 wherein $R^1$ and $R^2$ together are $—(CH_2)_2—C(=O)—(CH_2)_2—$ and $R^{1'}$ and $R^{2'}$ together are $—(CH_2)_2—CHOH—(CH_2)_2—$.

16. The process of claim 5 wherein $R^1$ and $R^2$ together are $—(CH_2)_2—C(=O)—(CH_2)_2—$ and $R^{1'}$ and $R^{2'}$ together are $—(CH_2)_2—CHOH—(CH_2)_2—$.

17. The process of claim 1 wherein $R^{2'}$ is phenyl.

18. The process of claim 4 wherein the carboxylic acid is acetic acid, the peroxy compound is hydrogen peroxide, the secondary alcohol is a cyclohexanediol and the oxidation is conducted in acetonitrile.

19. The process of claim 18 wherein the cyclohexanediol is 1,4-cyclohexanediol.

20. The process of claim 1 wherein the secondary alcohol is cyclohexanediol.

21. The process of claim 1 wherein $R^{1''}$ is a linear or branched $C_{1-10}$-alkyl and $R^{2''}$ is a linear or branched $C_{1-10}$-alkyl.

22. The process of claim 1 wherein the oxidation is conducted in a polar aprotic solvent.

23. The process of claim 22 wherein the polar aprotic solvent is acetonitrile.

24. The process of claim 1 wherein the oxidation is conducted at 0 to 40 °C.

25. The process of claim 1 wherein, after the oxidation has been conducted, a reducing agent is added to reduce any excess of the peroxide compound.

* * * * *